(12) United States Patent
Chang et al.

(10) Patent No.: US 9,301,869 B2
(45) Date of Patent: Apr. 5, 2016

(54) MULTI-LAYER FILM AND OSTOMY PRODUCT MADE THEREFROM

(75) Inventors: Moh-Ching Oliver Chang, Lake in the Hills, IL (US); Kevin M. Harrington, Libertyville, IL (US)

(73) Assignee: Hollister Incorporated, Libertyville, IL (US)

( * ) Notice: Subject to any disclaimer, the term of this patent is extended or adjusted under 35 U.S.C. 154(b) by 173 days.

(21) Appl. No.: 13/499,853

(22) PCT Filed: Nov. 3, 2010

(86) PCT No.: PCT/US2010/055286
§ 371 (c)(1),
(2), (4) Date: May 8, 2012

(87) PCT Pub. No.: WO2011/056861
PCT Pub. Date: May 12, 2011

(65) Prior Publication Data
US 2012/0232504 A1  Sep. 13, 2012

Related U.S. Application Data

(60) Provisional application No. 61/258,933, filed on Nov. 6, 2009.

(51) Int. Cl.
*A61F 5/44* (2006.01)
*A61F 5/445* (2006.01)
(Continued)

(52) U.S. Cl.
CPC .................. *A61F 5/445* (2013.01); *B32B 27/08* (2013.01); *B32B 27/32* (2013.01); *Y10S 493/933* (2013.01); *Y10T 428/24975* (2015.01); *Y10T 428/31746* (2015.04); *Y10T 428/31757* (2015.04)

(58) Field of Classification Search
CPC ......... A61F 5/445; B32B 27/08; B32B 27/32; Y10S 493/933

USPC .......... 428/34.1, 336, 35.2, 36.6, 474.8, 36.7; 604/332, 327, 317, 34.1, 336, 35.2, 604/36.6, 474.8, 36.7
See application file for complete search history.

(56) References Cited

U.S. PATENT DOCUMENTS 4,239,826 A  12/1980  Knott
4,254,169 A   3/1981  Schroeder
(Continued)

FOREIGN PATENT DOCUMENTS

DE  4100350 A1  4/1992
EP  0588667 A2  3/1994
(Continued)

OTHER PUBLICATIONS

International Search Report for PCT/US2010/055286, dated Jan. 10, 2011.
(Continued)

*Primary Examiner* — Tatyana Zalukaeva
*Assistant Examiner* — Andrew J Mensh
(74) *Attorney, Agent, or Firm* — Levenfeld Pearlsetin, LLC

(57) ABSTRACT

A multi-layer, chlorine-free film for use in an ostomy bag or pouch includes a barrier layer formed from a non-chlorine containing amorphous polyamide resin and a maleic anhydride modified olefin or an epoxy modified olefin. The barrier layer is substantially impermeable to malodor causing compounds. Tie layers are a maleic anhydride grafted resin and contact each side of the barrier layer. Inner layers contact respective tie layers. The inner layers are one of an ethylene propylene copolymer based resin, an ethylene-octene based resin and blends-thereof. Outer layers contact respective inner layers. Each outer layer is an ethylene vinyl acetate or ethylene methyl acrylate copolymer or a blend thereof, or a polypropylene-based resin and blend thereof. The film exhibits high tear strength and low noise levels.

16 Claims, 1 Drawing Sheet

(51) Int. Cl.
*B32B 27/08* (2006.01)
*A61M 1/00* (2006.01)
*B32B 1/08* (2006.01)
*B32B 27/32* (2006.01)

(56) References Cited

U.S. PATENT DOCUMENTS

| | | |
|---|---|---|
| 4,347,332 A | 8/1982 | Odorzynski et al. |
| 4,376,799 A | 3/1983 | Tusim |
| 4,400,428 A | 8/1983 | Rosenthal et al. |
| 4,451,599 A | 5/1984 | Odorzynski et al. |
| 4,611,019 A | 9/1986 | Lutzmann et al. |
| 4,615,922 A | 10/1986 | Newsome et al. |
| 4,710,182 A | 12/1987 | Bryson |
| 4,724,185 A | 2/1988 | Shah |
| 4,726,984 A | 2/1988 | Shah |
| 4,839,235 A | 6/1989 | Shah |
| 4,851,290 A | 7/1989 | Vicik |
| 4,906,495 A | 3/1990 | Martini et al. |
| 4,911,963 A | 3/1990 | Lustig et al. |
| 5,043,205 A | 8/1991 | Perazzo et al. |
| 5,053,259 A | 10/1991 | Vicik |
| 5,077,109 A | 12/1991 | Lustig et al. |
| 5,110,390 A | 5/1992 | Martini et al. |
| 5,330,454 A | 7/1994 | Klingler |
| 5,399,396 A | 3/1995 | Ohlsson et al. |
| 5,407,713 A | 4/1995 | Wilfong et al. |
| 5,455,091 A | 10/1995 | Oreglia et al. |
| 5,470,624 A | 11/1995 | Oreglia et al. |
| 5,496,295 A | 3/1996 | Wilfong et al. |
| 5,565,250 A | 10/1996 | Ohlsson et al. |
| 5,567,489 A | 10/1996 | Allen et al. |
| 5,582,820 A | 12/1996 | Yamamoto et al. |
| 5,618,276 A | 4/1997 | Leise, Jr. |
| RE35,567 E | 7/1997 | Newsome |
| 5,643,375 A | 7/1997 | Wilfong et al. |
| 5,658,625 A | 8/1997 | Bradfute et al. |
| 5,730,919 A | 3/1998 | Wilfong et al. |
| 5,895,694 A | 4/1999 | Zavadsky et al. |
| 5,983,604 A | 11/1999 | Wilfong et al. |
| 5,985,390 A | 11/1999 | DeGrand |
| 5,989,235 A * | 11/1999 | Quacquarella et al. ........ 604/332 |
| 6,011,115 A | 1/2000 | Miharu et al. |
| 6,068,933 A | 5/2000 | Shepard et al. |
| 6,143,383 A | 11/2000 | Giori |
| 6,258,423 B1 | 7/2001 | Giori |
| 6,291,041 B1 | 9/2001 | Howells et al. |
| 6,312,776 B1 | 11/2001 | Finkelstein et al. |
| 6,399,170 B1 | 6/2002 | Hock et al. |
| 6,455,161 B1 | 9/2002 | Regnier et al. |
| 6,500,514 B1 | 12/2002 | Blemberg et al. |
| 6,503,588 B1 | 1/2003 | Hayashi et al. |
| 6,562,476 B2 | 5/2003 | Shepard et al. |
| 6,599,639 B2 | 7/2003 | Dayrit et al. |
| 6,620,474 B1 | 9/2003 | Regnier et al. |
| 6,841,618 B2 | 1/2005 | Masuda |
| 6,942,927 B2 | 9/2005 | Shepard et al. |
| 6,964,816 B2 | 11/2005 | Schell et al. |
| 6,998,160 B2 | 2/2006 | Grund et al. |
| 7,270,860 B2 | 9/2007 | Giori |
| 7,316,833 B1 | 1/2008 | Galloway et al. |
| 7,354,654 B2 | 4/2008 | Masuda et al. |
| 7,393,593 B2 | 7/2008 | Roussos |
| 7,517,569 B2 | 4/2009 | Kreitman et al. |
| 7,581,942 B2 | 9/2009 | Richards et al. |
| 7,815,617 B2 | 10/2010 | Dircks et al. |
| 7,819,849 B2 | 10/2010 | Dircks et al. |
| 2002/0025394 A1 | 2/2002 | Bradfute et al. |
| 2002/0068140 A1 | 6/2002 | Finkelstein et al. |
| 2002/0188065 A1 * | 12/2002 | Kelch .............................. 525/66 |
| 2003/0017352 A1 | 1/2003 | Dayrit et al. |
| 2003/0064182 A1 | 4/2003 | Giori |
| 2004/0052911 A1 | 3/2004 | Grund et al. |
| 2004/0059306 A1 | 3/2004 | Tsal et al. |
| 2004/0228992 A1 | 11/2004 | Giori |
| 2005/0273064 A1 | 12/2005 | Dircks et al. |
| 2006/0142485 A1 | 6/2006 | Hoch et al. |
| 2006/0272767 A1 | 12/2006 | Kreitman et al. |
| 2007/0166491 A1 | 7/2007 | Kennedy et al. |
| 2007/4166490 | 7/2007 | Dey et al. |
| 2007/0237916 A1 | 10/2007 | Rasmussen et al. |
| 2008/0199645 A1 | 8/2008 | Julien |
| 2008/0269701 A1 | 10/2008 | Dircks et al. |
| 2009/0221718 A1 | 9/2009 | Ruoslahti et al. |
| 2010/0121290 A1 | 5/2010 | Rasmussen et al. |

FOREIGN PATENT DOCUMENTS

| | | |
|---|---|---|
| EP | 0700777 A1 | 3/1996 |
| EP | 1101605 A2 | 5/2001 |
| JP | 1070065 A | 3/1989 |
| JP | 2005054147 A | 3/2005 |
| WO | 9311938 A1 | 6/1993 |
| WO | 02058205 A1 | 10/2002 |

OTHER PUBLICATIONS

EP Search Report dated Apr. 24, 2014 for EP 10829019.8.
EP Search Report dated Oct. 22, 2012 for EP 12177420.

* cited by examiner

MULTI-LAYER FILM AND OSTOMY PRODUCT MADE THEREFROM

CROSS-REFERENCE TO RELATED APPLICATION DATA

This application claims the benefit of priority of Provisional U.S. Patent Application Ser. No. 61/258,933, filed Nov. 6, 2009 entitled, "MULTI-LAYER FILM AND OSTOMY PRODUCT THEREFROM."

BACKGROUND

The present disclosure relates to a multilayer film material, and more particularly to chlorine-free multi-layer films and bags and pouches for ostomy use made therefrom.

Gas and odor barrier films are known and widely used in the medical and food packaging industries. Many such films have a barrier layer that contains chlorine; other barrier layers are chlorine-free. Chlorine-containing barrier layers use, for example, copolymers of vinylidene chloride vinyl chloride (VDC-VC) copolymers) and vinylidene chloride methyl acrylate copolymer (VDC-MA copolymers). These chlorine-containing films have exceptionally high malodor-causing compound barrier properties and are typically not adversely affected by the presence of moisture. One drawback to the use of chlorine-containing compounds is that these compounds, generally, present environmental issues in disposal, for example, incineration of materials after use. Another drawback is that specialized equipment is required to process these materials due to the corrosive nature of the chlorine compounds.

Barrier layers of chlorine-free material include vinyl alcohol based polymers, for example, ethylene vinyl alcohol (EVOH) copolymers and poly(vinyl alcohol) (PVOH). Unfortunately, these materials have been found to have reduced barrier performance in the presence of humidity.

Ostomy products and other applications relating to the storage of bodily liquids are highly demanding and typically subject materials used in such products to high levels of moisture. At the same time, it is extremely important that the odor barrier properties of the material are and remain high throughout their useful life. In addition, it is imperative that the mechanical strength of the material is also high and remains high for a sufficiently long period of time for extended use of the product Other factors and properties that must also be considered in ostomy product use are the comfort of the material, as such products are worn next to the user's body, the flexibility of the material so that it conforms to the user's movements, and the quietness of the product so that wearing such a product is as audibly imperceptible as possible. The chlorine-containing materials possess these beneficial properties and qualities, but have the aforementioned environmental issues in disposal and processing.

In an effort to provide a film having the beneficial properties and characteristics of VDC-VC, VDC-MA and other chlorine-containing materials, without the detrimental effects of these chlorine-containing materials, various layered films have been composed of non-chlorine containing materials. One known film, disclosed in DE-A-4100350, is a seven layer chlorine-free film for packaging material for infusion solutions. The material is composed of a base material that is a coextruded film made of an ethylene-vinyl alcohol (EVOH) copolymer and two coating polyethylene (PE) layers onto which a PE layer and an EVOH copolymer layer are extrusion laminated.

One film used in food packaging, disclosed in EP-A-0588667, is a multiple layer film, moisture barrier material that includes a core layer made of an oxygen barrier material, such as an EVOH copolymer, two intermediate layers provided on the core layer of a propylene (PP) polymer or copolymer or a polymeric adhesive, such as a carboxylic acid or maleic anhydride-modified polyolefin such as polypropylene-based carboxylic acid or maleic anhydride-modified polyolefin. Moisture barrier layers are provided as a blend of a PP polymer or copolymer and a hydrocarbon resin, and outermost layers covering the outer surfaces are also PP polymer or copolymer.

One film used in the manufacture of ostomy pouches, disclosed in International application publication WO93/11938, is a five-layer barrier structure having a gas barrier layer, two moisture barrier layers and optionally one or more adhesive layers disposed therebetween. The moisture barrier layer is a mesophase PP-based material which contacts one or both of the sides of the gas barrier layer. The gas barrier layer is made of an EVOH copolymer.

Other multi-layer films, such as those disclosed in U.S. Pat. Nos. 4,239,826 and 4,254,169, which include an oxygen barrier layer formed of vinyl alcohol polymer or copolymers (e.g. PVOH, EVOH), and moisture barrier layers formed of partially hydrolyzed vinyl acetate polymer or copolymer, or modified polyolefins, are also known. Such films have been found to be useful in the manufacture of food packaging containers.

A five layer chlorine-free ostomy pouch film is also known. Such a film, which is disclosed in Giori, U.S. Pat. No. 7,270,860 and is incorporated herein in its entirety by reference, has a core odor barrier layer formed of a blend or a compound including amorphous polyamide, and anhydride-modified olefin polymer or copolymer. The film also includes two tie layers on both sides of the core layer and two EVA or EVA-based surface layers.

Still another film, disclosed in EP 0700777 B1, is a chlorine-free composition having a gas-barrier layer of a non-chlorine containing organic polymer which is substantially impermeable to oxygen, two tie layers each contacting one side of the barrier layer, an inner surface layer, an outer surface layer and two intermediate layers positioned between the surface layers and tie layers. The intermediate layers are an ethylene-propylene copolymer having a flexural modulus (measured according to ASTM D-882) of less than 200 MPa., preferably less than 150 MPa.

Although these films are chlorine free and thus, achieve the desired goal with respect to environmental safety, they do not fully achieve the desired combination of physical properties, including moisture and odor barrier characteristics, tear strength, comfort and "quietness".

Accordingly, there is a need for a chlorine-free, multi-layer film for use in ostomy products that provides a barrier for malodor causing compounds. Desirably, such a film and products made therefrom maintain high barrier performance characteristics even in high moisture applications, for prolonged periods of time. More desirably still, such a film and products made therefrom exhibit high tear strength, and the products exhibit "quietness" when in use.

BRIEF SUMMARY

Multilayer films according to various embodiments are chlorine-free films that can provide odor barrier, tear strength and quietness properties comparable or better than that of chlorine containing films for ostomy bags. Further, the multilayer films can surprisingly provide improved tear strength and improved appearance and textural ("look and feel") qualities over the prior chlorine-free multilayer films, such as those disclosed in Giori, U.S. Pat. No. 7,270,860, by including selected inner layers and using particular tie layer formulations that have a lower adhesion to the barrier layer.

In one aspect, a multi-layer, chlorine-free film is used in the fabrication of an ostomy bag or pouch. The film includes a barrier layer having first and second sides, tie layers, inner layers, and outer layers. The barrier layer is formed from a non-chlorine containing amorphous polyamide resin present in a concentration of about 65 percent to about 100 percent by weight of the barrier layer and a maleic anhydride modified olefin or an epoxy modified olefin, present in a concentration of about 0 percent to about 35 percent by weight of the barrier layer. Further, the barrier layer is substantially impermeable to malodor causing compounds. First and second tie layers are formed of a maleic anhydride grafted resin, wherein the resin is one or more of an ethylene-based copolymer, a propylene-based copolymer, an ethylene-octene polymer and a styrene block copolymer. Each tie layer contacts a side of the barrier layer. First and second inner layers are formed of one of an ethylene propylene copolymer (polypropylene elastomer) based resin, an ethylene-octene based resin and blends thereof. Each inner layer contacts a respective tie layer. First and second outer layers are formed of an ethylene vinyl acetate or ethylene methyl acrylate copolymer and blends thereof, and polypropylene-based resins and blends thereof. The outer layers contact a respective inner layer.

In another aspect, a chlorine-free, multilayer film includes a barrier layer, at least one tie layer, at least one inner layer, and at least one skin layer. The barrier layer is formed of amorphous polyamide resin present in a concentration of about 65 percent to about 100 percent by weight of the barrier layer and a maleic anhydride modified or glycidyl methacrylate grafted resin, present in a concentration of about 0 percent to about 35 percent by weight of the barrier layer. The barrier layer is substantially impermeable to malodor causing compounds. At least one inner layer is formed of one of an ethylene propylene copolymer (polypropylene elastomer) based resin, an ethylene-octene based resin and blends thereof. At least one tie layer is arranged between the barrier layer and the at least one inner layer to facilitate an adhesion between the barrier layer and the at least one inner layer. At least one tie layer is formed of a maleic anhydride modified resin or a glycidyl methacrylate grafted resin, wherein the resin is one or more of an ethylene-based copolymer, a propylene-based copolymer, an ethylene-octene polymer and a styrene block copolymer. Finally, at least one skin layer is arranged adjacent the at least one inner layer. The at least one inner layer is formed of an ethylene vinyl acetate or ethylene methyl acrylate copolymer and blends thereof, and polypropylene-based resins and blends thereof.

In yet another aspect, a chlorine-free multilayer film including a barrier layer, at least one skin layer, and at least one tie layer is provided. The barrier layer, which is substantially impermeable to malodor causing compounds, is formed of amorphous polyamide resin present in a concentration of about 65 percent to about 100 percent by weight of the barrier layer and a maleic anhydride modified or glycidyl methacrylate grafted resin, present in a concentration of about 0 percent to about 35 percent by weight of the barrier layer. The at least one skin layer includes an ethylene vinyl acetate or ethylene methyl acrylate copolymer and blends thereof, and polypropylene-based resins and blends thereof. The at least one tie layer is formed of a maleic anhydride modified resin including a maleic anhydride content of between about 0.030% and about 0.080% by weight, wherein the resin is one or more of an ethylene-based copolymer, a propylene-based copolymer, an ethylene-octene polymer and a styrene block copolymer. The at least one tie layer is arranged between the barrier layer and the at least one skin layer. In some embodiments, the film can also include at least one inner layer arranged between the at least one tie layer and the at least one skin layer. The at least one inner layer comprising one of an ethylene propylene copolymer (polypropylene elastomer) based resin, an ethylene-octene based resin and blends thereof. In such embodiments, the at least one tie layer facilitates an adhesion between the barrier layer and the at least one inner layer.

Any one of the above described multilayer film that has a barrier layer, at least one tie layer, and at least one skin layer can have a five-layer film construction including skin layer/tie layer/barrier layer/tie layer/skin layer. Any one of the above described multilayer film that has a barrier layer, at least one tie layer, at least one inner layer, and at least one skin layer can have five-layer film constructions including skin layer/tie layer/barrier layer/tie layer/inner layer. In some embodiments, the multilayer film can have a five-layer construction including inner layer/tie layer/barrier layer/tie layer/inner layer. Further, any one of above described multilayer film can have a seven-layer film construction including skin layer/ inner layer/tie layer/barrier layer/tie layer/inner layer/skin layer.

The multilayer film according to any one of above embodiments having an Elmendorf tear strength in the machine direction measured by ASTM D19222-09 of at least about 200 g/mil.

Further, any one of above described multilayer films can include the barrier layer formed of a blend of between about 75% and about 95% by weight of an amorphous polyamide, and between about 5% and about 25% by weight of an maleic anhydride grafted ethylene ethyl acrylate copolymer; and the at least one tie layer formed of a maleic anhydride grafted blend of ethylene-propylene rubber and polypropylene. The tie layers of such a multilayer film can have a maleic anhydride content of between about 0.030% and about 0.080% by weight.

Further, any one above described multilayer films can include the inner layer formed of a blend of an ethylene propylene copolymer and a polypropylene-elastomer, and the skin layer formed a blend comprising an ethylene vinyl acetate and a PP-elastomer.

Further, any one of above described multilayer films can be a seven-layer film having a skin layer/inner layer/tie layer/ barrier layer/tie layer/inner layer/skin layer construction. The multilayer film can have a total thickness between about 30 μm and about 130 μm, wherein the thickness of the two skin layers and the two inner layers is between about 70% and about 95% of the total thickness of the film. The multilayer film can include the barrier layer formed of a blend comprising between about 75% and about 95% by weight of an amorphous polyamide, and between about 5% and about 25% by weight of an maleic anhydride grafted ethylene ethyl acrylate copolymer or an maleic anhydride grafted ethylene methyl acrylate copolymer or a maleic anhydride grafted styrene-ethylene-butylene-styrene copolymer; the tie layers formed of a maleic anhydride grafted blend of ethylene-propylene rubber and polypropylene or a maleic anhydride grafted ethylene methyl acrylate copolymer or a blend comprising a maleic anhydride grafted blend of ethylene-propylene rubber and polypropylene or a maleic anhydride grafted ethylene methyl acrylate copolymer; the inner layers formed of an ethylene octene (EO)-plastomer or PP-elastomer or a blend comprising an EO-plastomer or PP-elastomer; and the skin layers formed of an ethylene vinyl acetate or a blend including ethylene vinyl acetate.

Further, any one of the above described multilayer film can be symmetrical about the barrier layer. The multilayer film can include the barrier layer having a thickness between about 2 μm and about 6 μm; the tie layers, each having the same thickness between about 2 μm and about 6 μm; the inner layers, each having the same thickness between about 6 μm and about 24 μm; the skin layers, each having the same thickness between about 6 μm and about 30 μm.

In yet another aspect, an ostomy pouch or collection device for bodily waste is formed of any one of the above described multilayer films. The ostomy pouch includes two side walls, the each of which is formed of the multilayer film, and a stoma-receiving opening on one of the side walls. The two side walls are heat sealed together along peripheral edges of the side walls to form the ostomy pouch.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
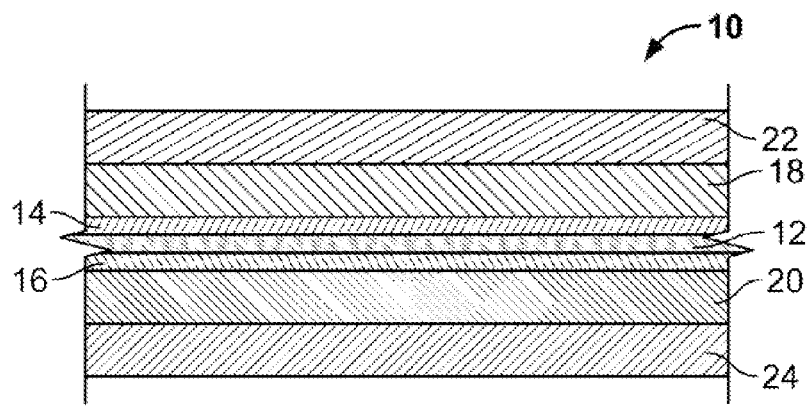
FIG. 1 is a cross-sectional illustration of a multilayer film according to an embodiment.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring now to the figures and in particular to FIG. 1, there is shown a chlorine-free multilayer film 10 according to an embodiment. The film 10 includes a gas-barrier layer 12 formed from a non-chlorine containing polymer that is substantially impermeable to malodor causing compound typically encountered in ostomy pouches. Such malodor causing compounds can include sulfur containing compounds and indoles. Examples of sulfur-containing compounds include dimethyl disulfide, dimethyl trisulfide, diethyl disulfide, hydrogen sulfide and methyl mercaptan. Examples of indoles, and other malodor causing compounds include 3-methyl indole and methanethiol. Other compounds will be recognized by those skilled in the art.

The film 10, as shown in FIG. 1, is a seven layer film. On either side of the barrier layer 12 is a tie layer 14, 16. The tie layers facilitate adhesion of the barrier layer to the remainder of the film structure. First and second inner layers 18, 20 are present adjacent to the tie layers 14, 16, respectively. The inner layers impart tear strength to the film, while at the same time facilitate achieving a "quiet", e.g. low dB(A) level, film. The outermost layers are seal and skin layers 22, 24, that are adjacent the first and second inner layers 18, 20, respectively. The seal and skin layers provide good heat sealing characteristics (to form a pouch or bag) and are also comfortable for application against a user's skin. The film thus has the structure ABCDCBA, where A represents the skin/seal layer, B represents the first and second inner layers, C represents the tie layers and D represents the barrier layer. Although the film 10 of this embodiment includes seven layers, in other embodiments, a multilayer barrier film can include more than seven layers or less than seven layers. For example, a multilayer film according to this disclosure can be a six-layer film including a barrier layer, two tie layers, an inner layer, and two skin layers (i.e. ABCDCA), or alternatively, a five-layer film including a barrier layer, two tie layers and two outer layers (i.e. ACDCA, BCDCB or ACDCB).

Barrier Layer

The barrier layer 12 can be formed from various materials. Suitable barrier layer materials include resins such as amorphous polyamide (nylon) resin, and an anhydride-modified olefinic polymer or copolymer, or an epoxy modified olefin polymer or copolymer. Such an amorphous polyamide has a partially aromatic structure and is typically produced by the condensation of an aliphatic diamine with an aromatic diacid, or combination of diacids, in molar amounts equivalent to the diamine used Partially aromatic nylons such as 6I/6T, MXDI/6I, MXD6/MXDI (wherein I is isophthalic acid, T is terephthalic acid, 6 is hexamethylenediamine, and MXD is metaxylenediamine) are suitable. While it is believed that a variety of amorphous polyamide resins may be used, effective results have been obtained with a polyamide resin marketed as Selar®, such as Selar® PA3426, by DuPont Company. Selar® PA3426 is understood to be substantially amorphous with a density of about 1.19 grams per cubic centimeter (g/cc) and a glass transition temperature (dry) of about 127° C. It has high melt strength and can be used under a broader range of processing conditions than conventional crystalline nylons.

An alternative amorphous nylon, having similar properties is Grivory®, such as Grivory® G21, which is commercially available from EMS-Chemie of Sumter, S.C. Grivory® G21 has a density of about 1.18 grams per cubic centimeter (g/cc) and a glass transition temperature (dry) of about 128° C. Another alternative amorphous nylon resin is Grivory® HB5299, which has a density of about 1.2 g/cc and a glass transition temperature (dry) of about 95° C. and a melting point temperature of about 219° C.

The barrier layer 12 can be formed of an amorphous polyamide resin compounded or blended with a maleic anhydride grafted blend of ethylene propylene rubber (EPR) and polypropylene (PP) (e.g. Zelas® MC721 AP from Mitsubishi); or maleic anhydride grafted or copolymerized ethylene methyl acrylate (EMA), ethylene vinyl acetate (EVA), ethylene butyl acrylate (EBA), ethylene ethyl acrylate (EEA) or other polyolefins (e.g. Lotader® 4720 from Arkema, Bynel® from DuPont, Plexar® form Lyondellbassell); or glycidyl methacrylate (GMA) grafted polyethylene (PE), EMA, or other polyolefins (e.g. Lotader® from Arkema); or maleic anhydride modified styrene-ethylene-butylene-styrene (SEBS) copolymer or other styrene block copolymers. In one preferred embodiment, the barrier layer 12 is formed of a blend of an amorphous polyamide and an anhydride-modified olefin polymer or copolymer. In such embodiment, the amorphous polyamide resin is the major constituent of the blend, comprising about 65% to about 100% by weight of that blend, preferably about 75% to about 95% by weight. The anhydride-modified olefinic polymer or copolymer comprises about 0% to about 35%, preferably about 5% to about 25% of the total weight of the barrier layer.

The anhydride-modified olefinic polymer or copolymer can be a copolymer of ethylene and at least one ester containing comonomer, or a blend thereof, modified (grafted or copolymerized) with about 0.01% to about 2% by weight of an unsaturated carboxylic anhydride (serving as a compatibilizing agent). The anhydride-modified olefinic polymer or copolymer can also be a copolymer of ethylene and an alpha-olefin, or a blend thereof, grafted or copolymerized with about 0.01% to about 2% of such anhydride.

The olefinic polymer or copolymers can be functionalized by copolymerization or grafting with an unsaturated carboxylic anhydride. While it is believed that other unsaturated carboxylic anhydrides may be used to provide the functional groups, maleic anhydride is considered particularly effective for that purpose. The level of maleic anhydride needed to functionalize the olefinic polymer is quite low, usually less than about 2% by weight.

One example of an anhydride-modified copolymer is formed from ethylene and at least one ester-containing comonomer, or a blend thereof, grafted or copolymerized with between about 0.01% to about 2% by weight of the unsaturated carboxylic anhydride, the anhydride content preferably being under about 0.5% by weight. The ester-containing comonomer is preferably an alkylacrylate, most preferably an ethylacrylate. One such copolymer is available from Arkema, Inc., of France, under the designation Lotader® 4720. Lotader® 4720 is an ethylene-ethyl acrylate-maleic anhydride terpolymer with a density of 0.944 g/cc, an ethyl acrylate content of about 30% by weight and a maleic anhydride content of about 0.3% by weight. Another such maleic anhydride grafter copolymer is an ethylene methyl acrylate-maleic anhydride polymer available from Arkema as Lotader® 4603.

Similar performance can be achieved with other anhydride-modified olefinic polymers of copolymers sharing comparable low density, such as ethylene-propylene copolymers, ethylene methyl acrylate copolymers, and terpolymer (EPM, EMA and EPDM). EPM and EPDM have a density in the 0.85 to 0.86 g/cc range and all are suitable for modification with maleic anhydride.

It has also been found that a blend of amorphous nylon and a maleic anhydride (MAH) grafted styrene-ethylene-butylene-styrene (SEBS) copolymer (the maleic anhydride present in a concentration of about 1.0 percent of the copolymer) is suitable for the barrier layer. In such a blend, the amorphous nylon is present in a ratio of about 85 percent by weight of the barrier layer and the MAH grafted SEBS copolymer is present in a concentration of about 15 percent by weight. Such resin provides the desired malodor barrier and tear strength characteristics. An exemplary SEBS copolymer is Kraton® FG1924, commercially available from Kraton Polymers US, LLC, and the amorphous nylon can be, for example, the above-noted Selar® PA3246.

It is also believed that functional groups other than MAH can be used in the barrier layer resins. For example, epoxy functional rubber can be used, such as glycidyl methacrylate (GMA) copolymerized with ethylene and other monomers. One such resin is ethylene-methyl acrylate glycidyl methacrylate (E-MA-GMA), available from Arkema as Lotader® AX8920, and ethylene-glycidyl methacrylate (E-GMA), also available from Arkema as Lotader® AX8840.

Tie Layers

The tie layers 14, 16 can be formed of the same material or different materials. In the embodiment of FIG. 1, the tie layers 14, 16 are formulated from the same material. Suitable materials for the tie layers include, but not limited to, MAH grafted blend of EPR and PP (e.g. Zelas® MC721 AP from Mitsubishi); MAH grafted or copolymerized EMA, EVA, EBA, EEA or other polyolefins (e.g. Lotader® from Arkema, Bynel® from DuPont, Plexar® from Lyondellbassell); MAH grafted polypropylene (PP) concentrate (e.g. Bynel® from DuPont) blend with ethylene-propylene copolymer (PP-elastomer) (e.g. Vistamaxx® from Exxon, Versify® from Dow), ethylene-octene (EO) plastomer (e.g. Exact® from Exxon, Affinity® from Dow), EMA (e.g. Lotryl® from Arkema), or other polyolefins; or GMA grafted PE, EMA or other polyolefins (e.g. Lotader® from Arkema.) An olefin-based thermoplastic elastomer (EPR rubber), MAH grafted EMA copolymers, blends of EMA and MAH grafted linear low density polyethylene (LLDPE), PE, EVA copolymers, or ethylene modified with functional anhydride groups are believed particularly suitable.

One suitable material for the tie layers is a blend of about 80 percent of an EMA copolymer having methyl acrylate present at about 18.5 percent by weight of the copolymer and about 20 percent of a MAH grafted linear low density polyethylene (LLDPE), having maleic anhydride present at about 0.8 percent to 1.1 percent of the MAH-LLDPE polymer. One such EMA polymer is available from Arkema, Inc. as Lotryl®18MA02. This resin has a melting point temperature of 87° C. and a Shore hardness of 25. One MAH grafted LLDPE is available from DuPont Company under the designation Bynel®CA41E710.

Still another suitable material is a MAH grafted ethylene methyl acrylate copolymers (EMA) having maleic anhydride present at about 0.3 percent and methyl acrylate present at about 20 percent of the resin. One such material is available from Arkema, Inc as Lotader®4503, and has a melting point temperature of 78° C. and a Shore D hardness of 25.

Another suitable material for the tie layers is a MAH grafted blend of EPR and PP available as Zelas® MC721AP, from Mitsubishi Chemical Co. This resin has a melting point temperature of 158° C., a Shore A hardness of 75 and a specific gravity of 0.89. This resin imparts a high mechanical strength and serves to tie or adhere the barrier layer to the inner and skin/seal layers.

Still another material that is anticipated to be suitable is an epoxy functional rubber, such as the above-noted glycidyl methacrylate (GMA) copolymerized with ethylene and other monomers, such as E-MA-GMA (Lotade® AX8920) and E-GMA (Lotader® AX8840).

Inner layers

The first and second inner layers, 18, 20 can be formulated from the same material or different materials. In the embodiment of FIG. 1, both of the first and second inner layers 18, 20 are formed of the same material. The inner layers 18, 20 impart mechanical (tear) strength to the film 10 and also impart quietness to the film 10. Ethylene based polymers, such as ethylene vinyl acetate (EVA) copolymer, ethylene-octene (EO) plastomers, and ethylene-propylene (EP) copolymers (PP-elastomer) are suitable film forming materials for the inner layers. One suitable material is an ethylene vinyl acetate (EVA) copolymer having a vinyl acetate content of about 8 percent to 30 percent and preferably about 10 percent to about 25 percent, a melting point temperature of about 86° C. and a Shore A hardness of about 91, such as Escorene®FL00218, available from ExxonMobil Corporation.

Another suitable material is an EO plastomer having a melting point temperature of about 95° C. and specific gravity of about 0.902, such as Exact® 0203 resin, also available from ExxonMobil Corporation, which has a specific gravity of about 0.88 and a Shore A hardness of about 95. This resin is designed for both monolayer and multilayer co-extruded cast film applications and is suitable in applications that require toughness and heat sealing performance. Typical applications include film for industrial packaging.

Still another suitable resin is an ethylene-propylene copolymer (PP-elastomer) resin that exhibits a low melt flow rate making it suitable for film application and heat sealing. It has a low modulus and thus exhibits low noise characteristics. It has excellent compatibility with PP and PE. One such material is available from Dow Chemical from as Versify®2200. This resin has melting point of about 82° C., a Shore A hardness of 94 and a Shore D hardness of 42. It has a specific gravity of 0.878. Blends of various PP copolymer resins have also been found to be suitable, for example, blends of Versify®2200 and Versify®3400, which is a similar PP copolymer resin, but has a higher melting point of about 97° C., a Shore A hardness of 72 and a Shore D hardness of 22, and a specific gravity of about 0.865. Suitable blends can have ratios of about 50 percent of Versify®2200 to about 75 percent of Versify®2200 by weight of the blend. PP-elastomers such as Versify® from Dow, Vistamaxx® from Exxon, and Notio® from Mitsui are also suitable.

Seal/Skin Layers

The seal and skin layers 22, 24 can likewise be formed of the same or different materials. In the embodiment of FIG. 1, the seal/skin layers 22, 24 are formed of the same material. These layers are typically formed of an ethylene-based polymer or copolymer. Suitable resins include, for example, copolymers of ethylene with vinyl esters, such as vinyl acetate copolymer (EVA) and copolymers of ethylene methyl acrylate (EMA). EVA copolymers contain about 10 percent to 35 percent vinyl acetate and more preferably, about 18 percent by weight vinyl acetate, by weight of the copolymer. One material is available from ExxonMobil as product Escorene® Ultra FL00218. Such a material has a melting point temperature of 86° C. and a Shore A hardness of about 91. EVA based materials provide increased comfort for the person using an ostomy pouch made from this material. EVA is also known to exhibit the necessary characteristics for joining to another EVA member, as by heat sealing, to provide an air-tight, liquid-tight seal at the joint or seal. EVA materials can be blended to facilitate formation and film extrusion. For example, an EVA blend can have about 98 percent by weight EVA with about 2 percent anti-block and slip additives, in an EVA carrier. One suitable additive is available from A. Schulman Inc., as Polybatch® SAB-1982VA.

EMA copolymers include about 10 to about 35 percent of the methyl acrylate and preferably about 18.5 percent to about 30 percent by weight methyl acrylate, by weight of the copolymer. Such EMA copolymers typically have melting point temperatures of about 85° C. to 87° C. and a Shore A hardness of about 73 and Shore D hardnesses of about 20 to 25. Suitable materials are available from Arkema Inc. as Lotryl®18AMO2 and from DuPont as Elvaloy®1330AC. The EMA resins can also be blended with anti-block and slip additives in an EVA carrier. One suitable material for blending is the aforementioned Polybatch® SAB-1982VA. Such a blend can have, for example EMA at about 98 percent by weight, with about 2 percent Polybatch® SAB-1982VA antiblock and slip additive.

As set forth above, other suitable seal and skin layers are formed as a blend of EVA copolymer (Escorene®FL00218 present at 49 percent) and PP-elastomer (Versify®2200 present at 49 percent) with anti-block and slip additives, and blends of EMA (Elvaloy®1330AC present at 49 percent) and PP-elastomer (Versify®2200 present at 49 percent) also with anti-block and slip additives. PP-elastomers such as Versify® from Dow, Vistamaxx® from Exxon, and Notio® from Mitsui are also suitable.

Multilayer Film

The multilayer films, such as the film 10, can be symmetrical films. That is, the layers on opposing sides of the barrier layer, namely the tie layers, inner layers and seal and skin layers are identical. The thicknesses of the various layers can also be identical. A preferred barrier layer has a thickness of about 2 microns to about 6 microns (μm); a preferred tie layer has a thickness of about 2 μm to about 6 μm; a preferred inner layer has a thickness of about 6 μm to about 24 μm; and a preferred seal/skin layer has a thickness of about 6 μm to about 30 μm. Accordingly, the overall film has a thickness of about 30 μm to about 126 μm. In one embodiment, the film 10 includes the barrier layer 12 having a thickness between about 3 μm and 5 μm, preferably about 4 μm; the tie layers 14, 16, each tie layer having a thickness between about 2 μm and 5 μm, preferably between about 3 μm and 4 μm; the inner layers 18, 20, each inner layer having a thickness between about 10 μm and about 17 μm, preferably between about 13 μm and about 15 μm; and the skin/seal layers 22, 24, each skin/seal layer having a thickness between about 12 μm and about 22 μm, preferably between about 18 μm and about 19 μm. Thus, the film 10 of this embodiment has a thickness between about 5 μm and about 93 μm, preferably between about 72 μm and about 80 μm.

A present film is formed as a coextruded sheet. It is anticipated that the different thermoplastic resins used for the barrier layer 12, the two tie layers 14, 16, the inner layers 18, 20 and the seal and skin layers 22, 24 will be fed continuously into respective extruders, melted in the extruders and transported from a feed-block or combining adaptor into a die where the different polymers, one layer over and adhering to the other, exit the die slot. Such a coextrusion process or another process for forming such a film will be recognized by those skilled in the art.

Figure 2:
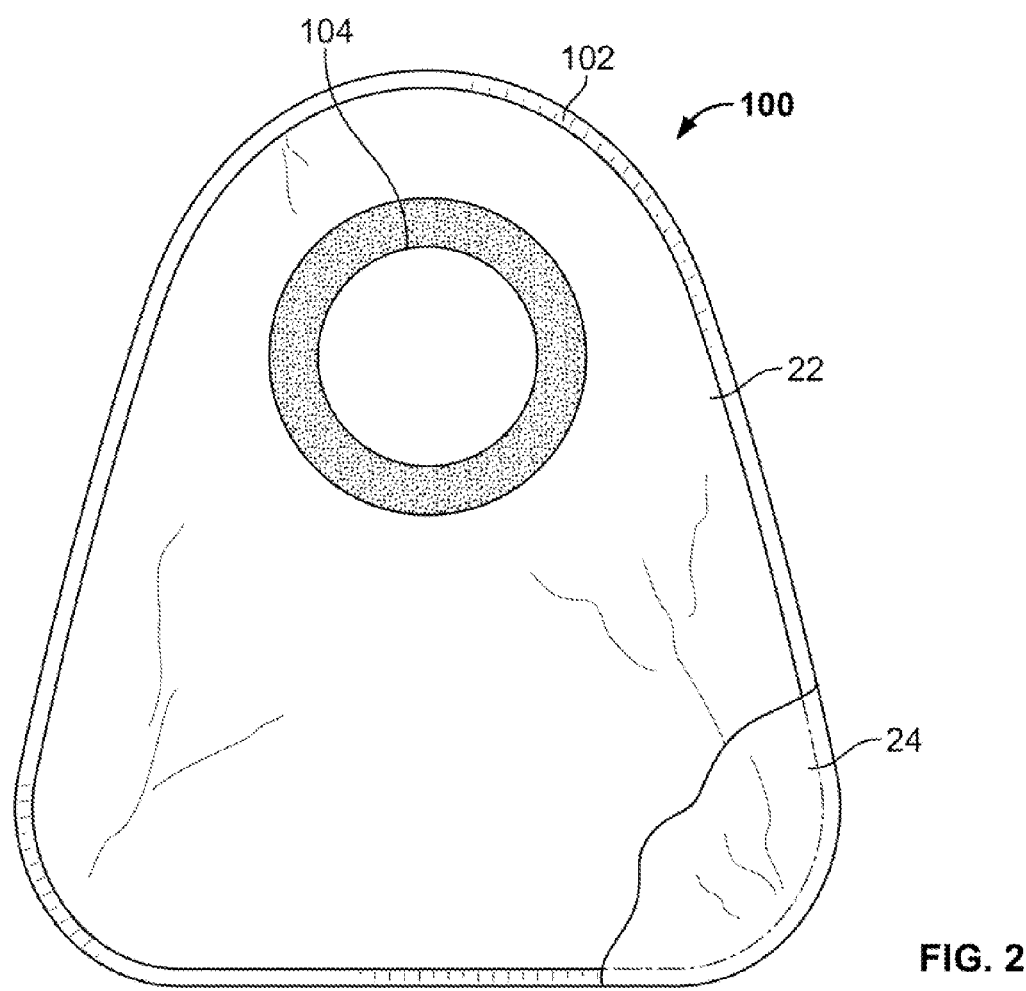
FIG. 2 is an illustration of an exemplary ostomy pouch.

The film 10 can be used to manufacture, for example, an ostomy bag or pouch 100, such as that illustrated in FIG. 2. The pouch is formed from two sheets of film that are heat or otherwise sealed, as at 102 to one another to form an air-tight, liquid-tight pouch. An opening 104 in the pouch permits the accommodation of, for example, a surgically formed stoma (not shown) for the inflow of waste into the pouch. The configuration of such a pouch can be in accordance with the disclosure of the aforementioned U.S. Pat. No. 7,270,860 to Giori. Other configurations of pouches or other containers, as well as other uses, will be recognized by those skilled in the art.

EXAMPLES AND TEST RESULTS

Multilayer Films

Several different seven-layer film samples were made using various combinations of resins for the barrier, tie, inner layers and sealskin layers. The Elmendorf tear strength in the machine direction (MD) in grams per mil and the noise level (sound pressure level) of the film in decibels (average) across the noise spectrum between 8 and 16000 Hz were measured. The results of the testing of the samples are provided in Table 1, below.

In the Control film, the barrier layer was formulated from a blend of an amorphous nylon (85 percent by weight Selar® PA3426) and an ethylene ethyl acrylate maleic anhydride copolymer (15 percent by weight Lotader® 4720). The tie layers were formulated from a blend of an EMA (80 percent by weight Lotryl® 18MA02) and MAH grafted LLDPE (20 percent by weight Bynel® CXA41E710). The inner layers were formulated from EVA (Escorene® FL00218) and the seal/skin layers were formulated from a blend of EVA (98 percent by weight Escorene® FL00218) with an anti-block and slip additive (2 percent Polybatch® SAB-1982VA).

In Sample 1, the barrier layer was formed from a blend of amorphous nylon (85 percent by weight Grivory® HB5299) and an SEBS copolymer (15 percent by weight Kraton® FG 1924), the tie layers were formulated from neat MAH grafted EMA copolymer (Lotader®4503), the inner layers were formulated from an EO plastomer (Exact® 0203) and the seal/skin layers were formulated from a blend of EMA copolymer (98 percent by weight Lotryl®18AM02) and anti-block and slip additives in an EVA carrier (2 percent Polybatch® SAB-1982VA).

In Sample 2, the barrier layer was formed from a blend of amorphous nylon (75 percent by weight Grivory® HB5299) and ethylene ethyl acrylate maleic anhydride copolymer (25 percent by weight Lotader® 4720), the tie layers were neat MAH grafted EMA copolymer (Lotader®4503), the inner layers were EO plastomer (Exact® 0203) and the seal/skin layers were a blend of EMA copolymer (98 percent by weight Lotryl®18AMO2) and anti-block and slip additives in an EVA carrier (2 percent Polybatch® SAB-1982VA).

In Sample 3, the barrier layer was formed from a blend of amorphous nylon (85 percent by weight Grivory® G21) and SEBS copolymer (15 percent by weight Kraton® FG1924), the tie layers were neat MAH grafted EMA copolymer (Lotader®4503), the inner layers were EO plastomer (Exact® 0203) and the seal/skin layers were a blend of EVA (98 percent by weight Escorene® FLO0218) with an anti-block and slip additive (2 percent Polybatch® SAB-1982VA).

In Sample 4, the barrier layer was formed from a blend of amorphous nylon (85 percent by weight Grivory® G21) and SEBS copolymer (15 percent by weight Kraton® FG 1924), the tie layers were neat MAH grafted blend of EPR and PP (Zelas® MC721AP), the inner layers were neat PP-elastomer (Versify® 2200) and the seal/skin layers were blended a blend of EVA (98 percent by weight Escorene® FLO0218) with an anti-block and slip additive (2 percent Polybatch® SAB-1982VA).

In Sample 5, the barrier layer was blended amorphous nylon (85 percent by weight Selar® PA3426) and ethylene ethyl acrylate maleic anhydride copolymer (15 percent by weight Lotader®4720), the tie layers were a blend of a EMA (80 percent by weight Lotryl® 18MA02) and MAH grafted LLDPE (20 percent by weight Bynel® CXA41E710), the inner layers were neat EO plastomer (Exact® 0203), and the seal/skin layers a blend of EVA (98 percent by weight Escorene® FL00218) with an anti-block and slip additive (2 percent Polybatch® SAB-1982VA).

In Sample 6, the barrier layer was blended amorphous nylon (75 percent by weight Selar® PA3426) and an MAH grafted EMA copolymer (25 percent by weight Lotader® 4603), the tie layers were neat MAH grafted EMA (Lotader® 4603), the inner layers were neat EU plastomer (Exact® 0203), and the sealskin layers were a blend of EVA (98 percent by weight Escorene® FL00218) with an anti-block and slip additive (2 percent Polybatch® SAB-1982VA).

In Sample 7, the barrier layer was blended amorphous nylon (80 percent by weight Selar® PA3426) and MAH grafted EMA copolymer (20 percent by weight Lotader® 4603), the tie layers were neat MAH grafted blend of EPR and PP (Zelas® MC721AP), the inner layers were neat PP-elastomer (Versify® 2200), and the seal/skin layers were a blend of EVA (98 percent by weight Escorene® FL00218) with an anti-block and slip additive (2 percent Polybatch® SAB-1982VA).

In Sample 8, the barrier layer was blended amorphous nylon (80 percent by weight Selar® PA3426) and ethylene ethyl acrylate maleic anhydride copolymer (20 percent by weight Lotader® 4720), the tie layers were neat MAH grafted blend of EPR and PP (Zelas®MC721AP), the inner layers were neat PP-elastomer (Versify® 2200), and the seal/skin layers were EMA (49 percent by weight Elvaloy®1330AC) and PP-elastomer (49 percent by weight Versify®2200) and anti-block and slip additives in an EVA carrier (2 percent Polybatch® SAB-1982VA).

In Sample 9, the barrier layer was blended amorphous nylon (80 percent by weight Selar® PA3426) and MAH grafted EEA copolymer (20 percent by weight Lotader® 4720), the tie layers were neat MAH grafted blend of EPR and PP (Zelas® MC721AP), the inner layers were neat PP-elastomer (Versify® 2200), and the seal/skin layers were a blend of EVA (49 percent by weight Escorene® FL00218) and PP-elastomer (49 percent by weight Versify®2200) with an anti-block and slip additive (2 percent Polybatch® SAB-1982VA).

In Sample 10, the barrier layer was blended amorphous nylon (75 percent by weight Selar® PA3426) and MAH grafted EMA copolymer (25 percent by weight Lotader® 4603), the tie layers were neat MAH grafted blend of EPR and PP (Zelas® MC721AP), the inner layers were neat PP-elastomer (Versify® 2200), and the sealskin layers were blended a blend of EVA (98 percent by weight Escorene® FL00218) with an anti-block and slip additive (2 percent Polybatch® SAB-1982VA).

The Elmendorf tear testing was conducted in accordance with Elmendorf Tear Performance as measured by ASTM D1922-09, Standard Test Method for Propagation Tear Resistance of Plastic Film and Thin Sheeting by Pendulum Method.

The film was tested for quietness by forming a 3.5 inch by 3.5 inch sample into a cylinder and mounting it on a test fixture wherein one end of the cylinder was held fixed and the other was rotated around the cylinder axis at an angle of 15 degrees at 70 cycles per minutes. Noise emissions produced by the film's flexing were analyzed with a digital sound level meter system. For comparison, the same test was conducted on a commercial ostomy film with a chlorinated barrier. Results are shown in Table 1, below as Noise SPL measured in dB(A). In the table, dB(A) is a weighted average that takes into account the human perception of noise over the entire frequency range, whereas dB values in the 8 and 16 kHz octave bands are indicative of the noise in the higher frequency range and represent the crispness of the noise.

TABLE 1

ELMENDORF TEAR STRENGTH AND NOISE LEVEL RESULTS FOR VARIOUS SEVEN LAYER FILMS

|  | Seal/Skin (each layer 19 μm) | Inner layers 1, 2 (each layer 13 μm) | Tie (each layer 4 μm) | Barrier | Elmendorf (MD) g/mil | Noise SPL dB(A)(see Note 1, below) |
|---|---|---|---|---|---|---|
| Control | 98% Escorene ® F00218 + 2% Schulman ® SAB1982VA | Escorene ® FL00218 | Blend: 80% Lotryl ® 18MA02 + 20% Bynel ® CXA41E710 | Blend: 85% Selar ® PA3426 + 15% Lotader ® 4720 | 14 | 63.1 |

TABLE 1-continued

ELMENDORF TEAR STRENGTH AND NOISE LEVEL RESULTS
FOR VARIOUS SEVEN LAYER FILMS

|  | Seal/Skin (each layer 19 μm) | Inner layers 1, 2 (each layer 13 μm) | Tie (each layer 4 μm) | Barrier | Elmendorf (MD) g/mil | Noise SPL dB(A)(see Note 1, below) |
|---|---|---|---|---|---|---|
| Sample 1 | 98% Lotryl ® 18MA02 + 2% Schulman ® SAB1982VA | Exact ® 0203 | Lotader ® 4503 | Precompound: 85% HB5299 + 15% Kraton ® FG1924 | 213 | 66.4 |
| Sample 2 | 98% Lotryl ® 18MA02 + 2% Schulman ® SAB1982VA | Exact ® 0203 | Lotader ® 4503 | Precompound: 75% HB5299 + 25% Lotader ® 4720 | 265 | 66.2 |
| Sample 3 | 98% Escorene ® FL00218 + 2% Schulman ® SAB1982VA | Exact ® 0203 | Lotader ® 4503 | Precompound: 85% G21 + 15% Kraton ® FG1924 | 311 | 66.3 |
| Sample 4 | 98% Escorene ® FL00218 + 2% Schulman ® SAB1982VA | Versify ® 2200 | Zelas ® MC712AP | Precompound: 85% G21 + 15% Kraton ® FG1924 | 491 | 66.5 |
| Sample 5 | 98% Escorene ® FL00218 + 2% Schulman ® SAB1982VA | Exact ® 0203 | Blend: 80% Lotryl ® 18MA02 + 20% Bynel ® CXA41E710 | Blend: 85% Selar ® PA3426R + 15% Lotader ® 4720 | 73 | 64.9 |
| Sample-6 | 98% Escorene ® FL00218 + 2% Schulman ® SAB1982VA | Exact ® 0203 | Lotader ® 4603 | Precompound: 75% Selar ® PA3426R + 25% Lotader ® 4603 | 426 | 64.8 |
| Sample 7 | 98% Escorene ® FL00218 + 2% Schulman ® SAB1982VA | Versify ® 2200 | Zelas ® MC712AP | Blend: 80% Selar ® PA3426R + 20% Lotader ® 4603 | 363 | 67.9 |
| Sample 8 | 49% Elvaloy ® 1330 + 49% Versify ® 2200 + 2% Schulman ® SAB1982VA | Versify ® 2200 | Zelas ® MC712AP | Precompound: 80% Selar ® PA3426R + 20% Lotader ® 4720 | 348 | 68.6 |
| Sample 9 | 49% Escorene ® FL00218 + 49% Versify ® 2200 + 2% Schulman ® SAB1982VA | Versify ® 2200 | Zelas ® MC712AP | Precompound: 80% Selar ® PA3426R + 20% Lotader ® 4720 | 349 | 65.8 |
| Sample 10 | 98% Escorene ® FL00218 + 2% Schulman ® SAB1982VA | Versify ® 2200 | Zelas ® MC712AP | Precompound: 75% Selar ® PA3426R + 25% Lotader ® 4603 | 513 | 65.9 |

Note 1
SPL dB(A): noise spectrum between 8 and 16000 Hz.

As can be seen from the results in Table 1, other than the Control film and the film of Sample 5, the multi-layer films all exhibited relatively high tear strength 213 to 513 g/mil and relatively low noise levels (inclusive of the Control and Sample 5 films). The performance of films having EO copolymer and PP based inner layers (again, except for the film of Sample 5), all exhibited acceptable tear strength and noise levels.

Monolayer Films

Ten samples (Samples 11 through 20) of monolayer films were also tested to determine the tear strength—(Elmendorf tear strength in the machine direction (MD) in grams per mil and in the transverse direction (TD), and the noise level (sound pressure level) of the film in decibels (average) across the noise spectrum between 8 and 16000 Hz were measured. The results of the testing of the monolayer samples are provided in Table 2, below.

TABLE 2

ELMENDORF TEAR STRENGTH AND NOISE LEVEL RESULTS FOR VARIOUS MONOLAYER FILMS

|  | Monolayer Blend | Elmendorf (MD) g/mil | Elmendorf (TD) g/mil | Noise SPL dB(A) (see Note 1 above) |
|---|---|---|---|---|
| Sample 11 | 98% Escorene ® FL00218 + 2% Schulman ® SAB1982VA | 215 | 227 | 56.6 |
| Sample 12 | 98% Exact ® 0203 + 2% Schulman ® SAB1982VA | 360 | 381 | 56.6 |
| Sample 13 | 49% Escorene ® FL00218 + 49% Exact ® 0203 + 2% Schulman ® SAB1982VA | 187 | 447 | 54.6 |
| Sample 14 | 98% Affinity ® PL 1800G + 2% Schulman ® SAB1982VA | 207 | 296 | 55.5 |
| Sample 15 | 73.5% Affinity ® PL 1800G + 24.5% Affinity ® EG8100 + 2% Schulman ® SAB1982VA | 161 | 285 | 54.8 |
| Sample 16 | 73.5% Exact ® 0203 + 24.5% Affinity ® EG8100 + 2% Schulman ® SAB1982VA | 233 | 385 | 56.6 |
| Sample 17 | 58.8% Affinity ® EG8100 + 39.2% Sclair ® FP120-C + 2% Schulman ® SAB1982VA | 132 | 222 | 62.5 |
| Sample 18 | 73.5% Escorene ® FL00218 + 24.5% Styroflex ® 2G66 + 2% Schulman ® SAB1982VA | 142 | 99 | 58.8 |
| Sample 19 | 49% Versify ® 3401 + 49% Versify ® 2200 + 1% Schulman ® SPER6SC + 1% Schulman ® ABPP10SC | 351 | 336 | 61.7 |
| Sample 20 | 24.5% Versify ® 3401 + 73.5% Versify ® 2200 + 1% Schulman ® SPER6SC + 1% Schulman ® ABPP10SC | 550 | 528 | 65.4 |

The resins that were used to form the monolayer films that were tested included those resins listed in Table 1 for the seven layer film and, in addition, also included a number of ethylene-octene (EO) plastomers, such as Affinity®PL 1880G (melting point temperature of 99° C., specific gravity of 0.902), and Affinity®EG8100G (melting point temperature of 55° C., Shore A hardness of 74 specific gravity of 0.872), both available from Dow Chemical, a linear low density polyethylene (LLDPE), such as Sclair® FP-120C (specific gravity of 0.922), available from Nova Chemicals, and a styrene block copolymer, such as Styroflex® 2G66 (having 65 percent styrene and a Shore A hardness), available from BASF Corporation. These resins were incorporated into blends in the monolayer films to determine their effectiveness in use in films to increase tear strength and reduce noise levels of the films.

In the monolayer films of Samples 19 and 20, the antiblock and slip additive (Polybatch® SAB-1982VA, 2 percent by weight) was replaced with Polybatch® SPER6SC (1 percent by weight), a polypropylene homopolymer slip agent and Polybatch® ABPP10SC (1 percent by weight), a synthetic silica (10 percent) in homopolymer PP anti-block agent.

As with the multi layer film testing, the monolayer film tear strength, was tested using Elmendorf Tear Performance in accordance with and as measured by ASTM D1922-09, Standard Test Method for Propagation Tear Resistance of Plastic Film and Thin Sheeting by Pendulum Method. Also as with the multi layer film, the monolayer film was tested for quietness by forming a 3.5 inch by 3.5 inch sample into a cylinder and mounting it on a test fixture wherein one end of the cylinder was held fixed and the other was rotated around the cylinder axis at an angle of 15 degrees at 70 cycles per minutes. Noise emissions produced by the film's flexing were analyzed with a digital sound level meter system. For comparison, the same test was conducted on a commercial ostomy film with a chlorinated barrier. Results are shown in Table 2, above, as Noise SPL measured in dB(A). In the table, dB(A) is a weighted average that takes into account the human perception of noise over the entire frequency range, whereas dB values in the 8 and 16 kHz octave bands are indicative of the noise in the higher frequency range and represent the crispness of the noise.

Multilayer Films Having Improved Tear Strength

Some of the multilayer films including tie layers having a lower adhesion between the tie layer and the barrier layer surprisingly exhibited a higher Elmendorf tear strength than multilayer films having comparably higher adhesion between the tie layer and the barrier layer. Four multilayer film samples, each including a different tie layer formulation having different adhesion strength, were prepared and tested for the Elmendorf tear strength. All four multilayer film samples were seven-layer films having a similar film construction as the film 10 of FIG. 1. Each of the multilayer film samples included a barrier layer having a thickness of about 4 μm formed of a blend of about 85% wt. of amorphous polyamide (Selar® PA3426R) and about 15% wt. of MAH grafted EEA copolymer (Lotader® 4720); two tie layers, each tie layer having a thickness of about 3 μml formed of a MAH grafted blend of EPR and PP, wherein an amount of MAH in the tie layer formulation is varied for each sample; two inner layers, each inner layer having a thickness of about 15 μm formed of about 65% wt. PP elastomer (Vistamaxx® 3980FL) and about 35% wt. propylene ethylene copolymer (Adflex® Q100F); and two skin/seal layers, each skin/seal layer having a thickness of about 18 μm formed of about 48.5% wt. EVA (Escorene® FL00218), about 48.5% wt. PP elastomer (Vistamaxx® 3980FL), about 2% wt. anti-block and slip additive (Schulman® SAB1982VA), and about 1% wt. processing aid (Schulman® AMF705.) Elmendorf tear strength test results in the machine direction (MD) of the samples are shown in Table 3, below.

TABLE 3

ELMENDORF TEAR STRENGTH (MD) OF SEVEN-LAYER FILMS INCLUDING VARYING TIE LAYER FORMULATIONS

| Seven-layer Film Sample Code | Amount of MAH in Tie Layer Formulation | Elmendorf Tear Strength (MD) g/mil |
|---|---|---|
| R5074 | 0.030% | 260 |
| R5076 | 0.045% | 201 |
| R5075 | 0.060% | 79 |
| R5061 | 0.080% | 37 |

As shown in Table 3, the film sample R5074 includes tie layers formed of a MAH grafted blend of EPR and PP, wherein the amount of MAH in the tie layer formulation is about 0.030% wt. Similarly, the film samples R5076, R5075, and R5061 include tie layers formed of a MAH grafted blend of EPR and PP, wherein the amount of MAH in the tie layer formulation is about 0.045% wt., about 0.060% wt., about 0.080% wt., respectively. In these tie layer formulations, an adhesion between the tie layer and the barrier layer increases as the amount of MAH increases (i.e. the tie layer formulation of sample R5061 with about 0.080% wt. MAH has the strongest adhesion between the tie layer and the barrier layer, while the tie layer formulation of sample R5074 with about 0.030% wt. MAH has the weakest adhesion between the tie layer and the barrier layer.) Surprisingly, as shown in Table 3, the Elmendorf tear strength of the seven-layer film samples in the machine direction increased with decreasing MAH amount in the tie layer and with decreasing adhesion strength of the tie layer. The tie layer formulations of MAH grafted blend of EPR and PP including MAH amount of less than about 0.080% wt., and particularly MAH amount of between about 0.030% wt. and about 0.080% wt., and more particularly MAH amount of between about 0.030% wt. and about 0.050% wt. are preferred as these formulations provide improved film tear strength.

Other seven-layer film constructions were tested for Elmendorf tear strength in machine direction, the results of which are listed in Table 4 below

TABLE 4

ELMENDORF TEAR STRENGTH OF SEVEN-LAYER FILMS

| Sample Code | Seal/Skin layers | Inner layers | Tie Layers | Barrier | Elmendorf Tear (MD) g/mil | Adhesion between Tie and Barrier N/15 mm |
|---|---|---|---|---|---|---|
| 260-2 | 19 μm 48.5% Escorene® FL00218 + 48.5% Versify® 2200 + 2% Schulman® SAB1982VA + 1% Schulman® AMF705 | 13 μm Versify® 2200 | 4 μm Zelas® MC721AP | 4 μm Blend: 85% Saler® PA3426R + 15% Lotader® 4720 | 22 | — |
| 260-3 | 19 μm 48.5% Escorene® FL00218 + 48.5% Versify® 2200 + 2% Schulman® SAB1982VA + 1% Schulman® AMF705 | 13 μm Versify® 2200 | 4 μm 50% Zelas® MC721AP + 50% Zelas® 7023 | 4 μm Blend: 85% Selar® PA3426R + 15% Lotader® 4720 | 239 | — |
| 264-2 | 18 μm 48.5% Escorene® FL00218 + 48.5% Vistamaxx® 3980FL + 2% Schulman® SAB1982VA + 1% Schulman® AMF705 | 15 μm 65% Vistamaxx® 3980FL + 35% Adflex® Q100F | 3 μm Zelas® MC721AP | 4 μm Blend: 85% Selar® PA3426R + 15% Lotader® 4720 | 41 | 4.7 |
| 264-3 | 18 μm 48.5% Escorene® FL00218 + 48.5% Vistamaxx® 3980FL + 2% Schulman® SAB1982VA + 1% Schulman® AMF705 | 15 μm 65% Vistamaxx® 3980FL + 35% Adflex® Q100F | 3 μm 75% Zelas® MC721AP + 25% Vistamaxx® 3980FL | 4 μm Blend: 85% Selar® PA3426R + 15% Lotader® 4720 | 318 | 2.4 |

All film samples in Table 4 are symmetrical seven-layer films similar to the film 10 of FIG. 1. Each of the film samples is constructed such that each of the tie layers has the same thickness and formed of the same material, each of the inner layers has the same thickness and formed of the same material, and each of the seal/skin layers has the same thickness and formed of the same material.

Sample film 260-2 is a seven-layer film having a total thickness of about 76 μm. The film includes a 4 μm thick barrier layer formed of a blend of about 85% wt. amorphous polyamide (Selar® PA3426R) and about 15% wt. MAH grafted EEA copolymer (Lotader® 4720); two tie layers, each having a thickness of about 4 μm and formed of MAH grafted blend of EPR and PP (Zelas® MC721AP); and two inner layers, each having a thickness of about 13 μm and formed of PP-elastomer (Versify® 2200); and two skin/seal layers, each having a thickness of about 19 μm and formed of about 48.5% wt. EMA (Escorene® FL00218), about 48.5% wt. PP-elastomer (Versify® 2200), about 2% wt anti-block and slip additive (Schulman® SAB1982VA), and about 1% wt. processing aid (Schulman® AMF705.) Sample film 260-3 is constructed similarly as Sample film 260-2, except the tie layer formulation has been altered to reduce the adhesion between the tie layer and the barrier layer. Each of the tie layers of Sample 260-3 is formed of a blend of two different MAH grafted blend of EPR and PP formulations (50% wt. Zelas® MC721AP and 50% wt. Zelas® 7023.) As shown in Table 4, Sample 260-3 including the reduced adhesion tie layer formulation resulted in an Elmendorf Tear strength in machine direction of 239 g/mil, which is significantly higher than that of Sample 260-2 having 22 g/mil.

Sample film 264-2 is also a seven-layer film having a total thickness of about 76 μm. The film includes a 4 μm thick barrier layer formed of a blend of 85% wt. amorphous polyamide (Selar® PA3426R) and 15% wt. MAH grafted EEA copolymer (Lotader® 4720); two tie layers, each having a thickness of about 3 μm and formed of MAH grafted blend of EPR and PP (Zelas® MC721AP); and two inner layers, each having a thickness of about 15 μm and formed of 65% wt. PP-elastomer (Vistamaxx® 3980FL) and 35% wt. propylene ethylene copolymer (Adflex® Q100F); and two skin/seal layers, each having a thickness of about 18 μm and formed of 48.5% wt. EMA (Escorene® FLO0218), 48.5% wt. PP-elastomer (Vistamaxx® 3980FL), 2% wt. anti-block and slip additive (Schulman® SAB1982VA), and 1% wt. processing aid (Schulman® AMF705.) Sample film 264-3 is constructed similarly as Sample film 264-2, except each of the tie layers of Sample 264-3 is formed of 75% wt. MAH grafted blend of EPR and PP (Zetas® MC721AP) and 25% wt. PP-elastomer (Vistamaxx® 3980FL). As shown in Table 4, an adhesion between the tie layer and the barrier layer of Sample film 264-3 was lower than that of Sample film 264-2. Accordingly, Sample film 264-3 had a significantly higher Elmendorf tear strength in machine direction than that of Sample film 264-3.

Panel Test

A seven-layer film was evaluated for qualitative "look and feel" by a test panel along with other films for ostomy pouches commercially available. The test panel consisted of 9 persons, who are either nurses working closely with ostomy patients or marketing professionals with an in-depth knowledge of ostomy patients' needs and wants.

Each of the panel members was provided with a sample of conventional ostomy pouch film including a PVDC copolymer barrier layer; a sample of another ostomy pouch film including PVDC copolymer barrier layer, which is commercially available as a "quiet" film; a sample of chlorine-free film disclosed in U.S. Pat. No. 7,270,860, which is commercially available through the assignee of the present application; and a sample of a present seven-layer film. The seven layer film sample had a similar construction as the film 10 of FIG. 1, and included a 4 μm thick barrier layer formed of a blend of 85% wt. amorphous polyamide (Selar® PA3426R) and 15% wt. MAH grafted EEA copolymer (Lotader® 4720); two tie layers, each having a thickness of about 4 μm and formed of MAH grafted blend of EPR and PP (Zelas® MC721AP); and two inner layers, each having a thickness of about 13 μm and formed of PP-elastomer (Versify® 2200); and two skin/seal layers, each having a thickness of about 19 μm and formed of 48.5% wt. EMA (Escorene® FLO0218), 48.5% wt. PP-elastomer (Versify® 2200), 2% wt. anti-block and slip additive (Schulman® SAB1982VA), and 1% wt. processing aid (Schulman® AMF705.)

Each sample was cut to a 8.5"×11" sheet marked with a sample number, but unidentified with the source (i.e. panel members did not know the construction or source of each sample.) The panel members were requested to evaluate each sample in the look and feel categories shown in Table 5 and rank each sample using 1-10 scale, 1 being poor and 10 being good. The panel evaluation results are shown in Table 5 below.

TABLE 5

| | Panel Look and Feel Test Results | | | | |
|---|---|---|---|---|---|
| | Ranking: 1-5-10 Poor-Medium-Good | Film w/ PVDC | Quiet film w/ PVDC | 7-layer film | U.S. Pat. No. 7,270,860 film |
| LOOK | clear <---------------> translucent | 5.6 | 7.4 | 6.9 | 5.0 |
| | shiny <--------------------------> dull | 4.6 | 7.1 | 7.0 | 3.6 |
| | suitable embossed depth | 4.6 | 6.8 | 7.5 | N/A |
| | cheap <-------------------> high value | 5.4 | 6.9 | 6.8 | 4.1 |
| FEEL | noise, crinkly sound <------> quiet, dull sound | 4.0 | 5.6 | 5.0 | 3.1 |
| | high pitch <-------------------> low pitch | | | | |
| | suitable embossed depth | 4.6 | 7.1 | 7.8 | N/A |
| | flimsy <-------------------> rubbery | 4.9 | 7.1 | 7.1 | 4.5 |
| | light, thin <---------------> heavy, thick | 5.6 | 7.4 | 7.0 | 5.3 |
| | cheap <-------------------> high value | 5.3 | 6.8 | 6.4 | 3.6 |
| | low tear strength <---------> high tear strength | 4.6 | 4.5 | 5.6 | 3.3 |
| | TOTAL | 49 | 67 | 67 | 33 |

As shown in Table 5, the present seven-layer film scored comparable with the "quiet" film including a PVDC barrier layer, and significantly better than the conventional ostomy pouch film including a PVDC barrier layer or the film according to U.S. Pat. No. 7,270,860 (the film according to U.S. Pat. No. 7,270,860 was not evaluated for embossing depth, as the sample did not include embossing. However, even if each embossing category was given the highest score of 10, the total score of the film according to U.S. Pat. No. 7,270,860 would have a maximum score of 43, still significantly lower than the present seven-layer film's total score.)

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A multi-layer, chlorine-free film for use in an ostomy bag or pouch, comprising:
a barrier layer having first and second sides, the barrier layer formed from a blend comprising a non-chlorine containing amorphous polyamide resin present in a concentration of about 75 percent to about 95 percent by weight of the barrier layer and a maleic anhydride modified olefin or an epoxy modified olefin, present in a concentration of about 5 percent to about 25 percent by weight of the barrier layer, the barrier layer being substantially impermeable to malodor causing compounds;
first and second tie layers, the tie layers comprising a maleic anhydride grafted resin, the resin being one or more of an ethylene-based copolymer, a propylene-based copolymer, an ethylene-octene polymer and a styrene block copolymer, each tie layer contacting a side of the barrier layer, wherein the amount of maleic anhydride is between 0.030% and 0.080% by weight of the tie layer;
first and second inner layers, the inner layers comprising one of an ethylene propylene copolymer based resin, an ethylene-octene based resin, and ethylene vinyl acetate, each inner layer contacting a respective tie layer; and
first and second outer layers, each outer layer comprising an ethylene vinyl acetate, ethylene methyl acrylate copolymer, or polypropylene-based resins, the outer layers contacting a respective inner layer.

2. The film in accordance with claim 1 wherein the film is symmetrical about the barrier layer.

3. The film in accordance with claim 1 wherein the barrier layer is formed from a blend comprising an amorphous nylon and a maleic anhydride modified ethylene ethyl acrylate copolymer.

4. The film in accordance with claim 1, wherein the multilayer film has an Elmendorf tear strength in machine direction measured by ASTM D19222-09 of at least about 200 g/mil.

5. The film accordance with claim 1, wherein each of the tie layer is formed of a maleic anhydride grafted blend of ethylene-propylene rubber and polypropylene.

6. The film accordance with claim 1, wherein the barrier layer is formed of a blend comprising between about 75% and about 95% by weight of an amorphous polyamide, and between about 5% and about 25% by weight of an maleic anhydride grafted ethylene ethyl acrylate copolymer or an maleic anhydride grafted ethylene methyl acrylate copolymer or a maleic anhydride grafted styrene-ethylene-butylene-styrene copolymer; wherein each of the tie layers is formed of a maleic anhydride grafted blend of ethylene-propylene rubber and polypropylene or a maleic anhydride grafted ethylene methyl acrylate copolymer or a blend comprising a maleic anhydride grafted ethylene-propylene rubber filled polypropylene copolymer or a maleic anhydride grafted ethylene methyl acrylate copolymer; wherein each of the inner layers is formed of an EO-plastomer or PP-elastomer or a blend comprising an EO-plastomer or PP-elastomer; and wherein each of the skin layers is formed of an ethylene vinyl acetate or a blend including ethylene vinyl acetate.

7. The film accordance with claim 1, wherein the film has a total thickness between about 30 μm and about 130 μm, wherein the thickness of the two skin layers and the two inner layers comprises between about 70% and about 95% of the total thickness of the film.

8. An ostomy pouch formed of the multilayer film of claim 1, comprising:
two side walls, wherein the each of the side walls is formed of the multilayer film of claim 1;
a stoma-receiving opening on one of the side walls; and
wherein the two side walls are heat sealed together along peripheral edges of the side walls.

9. A chlorine-free multilayer film, comprising:
a barrier layer formed from a blend comprising amorphous polyamide resin present in a concentration of about 75 percent to about 95 percent by weight of the barrier layer and a maleic anhydride modified or glycidyl methacrylate-grafted resin, present in a concentration of about 5 percent to about 25 percent by weight of the barrier layer, the barrier layer being substantially impermeable to malodor causing compounds;
at least one inner layer, the at least one inner layer comprising one of an ethylene propylene copolymer based resin, an ethylene-octene based resin and ethylene vinyl acetate;
at least one tie layer arranged between the barrier layer and the at least one inner layer, the at least one tie layer facilitating an adhesion between the barrier layer and the at least one inner layer, the at least one tie layer formed of a maleic anhydride modified resin, the resin being one or more of an ethylene-based copolymer, a propylene-based copolymer, an ethylene-octene polymer and a styrene block copolymer, wherein the amount of maleic anhydride is between 0.030% and 0.080% by weight of the tie layer; and
at least one skin layer arranged adjacent the at least one inner layer, the at least one skin layer comprising an ethylene vinyl acetate, ethylene methyl acrylate copolymer or polypropylene-based resins.

10. The film of claim 9, wherein the film has an Elmendorf tear strength in machine direction measured by ASTM D19222-09 of at least about 200 g/mil.

11. The film of claim 9, wherein the barrier layer is formed of a blend of between about 75% and about 95% by weight of an amorphous polyamide, and between about 5% and about 25% by weight of an maleic anhydride grafted ethylene ethyl acrylate copolymer; and the at least one tie layer is formed of a maleic anhydride grafted blend of ethylene-propylene rubber and polypropylene.

12. The film of claim 9, wherein the at least one inner layer is formed of a blend of a propylene ethylene copolymer and a polypropylene-elastomer.

13. The film of claim 9, wherein the at least on skin layer is formed a blend comprising an ethylene vinyl acetate and a PP-elastomer.

14. The film of claim 9, wherein the film is a seven-layer film having a skin layer/inner layer/tie layer/barrier layer/tie layer/inner layer/skin layer construction; the film having a total thickness between about 30 μm and about 130 μm, wherein the thickness of the two skin layers and the two inner layers is between about 70% and about 95% of the total thickness of the film.

15. The film of claim 9, wherein the barrier layer is formed of a blend comprising between about 75% and about 95% by weight of an amorphous polyamide, and between about 5% and about 25% by weight of an maleic anhydride grafted ethylene ethyl acrylate copolymer or an maleic anhydride grafted ethylene methyl acrylate copolymer or a maleic anhydride grafted styrene-ethylene-butylene-styrene copolymer; each of the tie layers is formed of a maleic anhydride grafted blend of ethylene-propylene rubber and polypropylene or a maleic anhydride grafted ethylene methyl acrylate copolymer or a blend comprising a maleic anhydride grafted ethylene-propylene rubber filled polypropylene copolymer or a maleic anhydride grafted ethylene methyl acrylate copolymer; each of the inner layers is formed of an EO-plastomer or PP-elastomer or a blend comprising an EO-plastomer or PP-elastomer; and each of the skin layers is formed of an ethylene vinyl acetate or a blend including ethylene vinyl acetate.

16. The film of claim 9, wherein the film is symmetrical about the barrier layer; wherein the barrier layer has a thickness between about 2 μm and about 6 μm; wherein each of the tie layers has a same thickness between about 2 μm and about 6 μm; wherein each of the inner layers has a same thickness between about 6 μm and about 24 μm; and wherein each of the skin layers has a same thickness between about 6 μm and about 30 μm.

* * * * *

UNITED STATES PATENT AND TRADEMARK OFFICE
CERTIFICATE OF CORRECTION

PATENT NO. : 9,301,869 B2
APPLICATION NO. : 13/499853
DATED : April 5, 2016
INVENTOR(S) : Chang et al.

Page 1 of 1

It is certified that error appears in the above-identified patent and that said Letters Patent is hereby corrected as shown below:

On the title page item [74], delete "Pearlsetin" insert --Pearlstein--.

In the specification

Column 1, line 46, delete "product" insert --product.--.

Column 6, line 50, delete "Lyondellbassell" insert --Lyondellbasell--.

Column 7, line 65, delete "Lyondellbassell" insert --Lyondellbasell--.

Column 8, line 37, delete "Lotade" insert --Lotader--.

Column 10, line 48, delete "sealskin" insert --seal/skin--.

Column 11, line 46, delete "sealskin" insert --seal/skin--.

Column 12, line 30, delete "sealskin" insert --seal/skin--.

Column 20, line 4, delete "Zetas" insert --Zelas--.

Signed and Sealed this
Fifth Day of July, 2016

Michelle K. Lee
*Director of the United States Patent and Trademark Office*